United States Patent [19]

Towle

[11] Patent Number: 5,041,611
[45] Date of Patent: Aug. 20, 1991

[54] PREPARATION OF MONOMERS

[75] Inventor: Ian D. H. Towle, Criencester, England

[73] Assignee: Raychem Limited, England, England

[21] Appl. No.: 355,935

[22] Filed: May 23, 1989

Related U.S. Application Data

[62] Division of Ser. No. 204,650, Jul. 29, 1988, Pat. No. 4,841,094, which is a division of Ser. No. 877,658, Jun. 3, 1986, Pat. No. 4,777,282.

[30] Foreign Application Priority Data

Aug. 27, 1985 [GB] United Kingdom ................. 8521324

[51] Int. Cl.$^5$ ...................... C07C 69/76; C07C 5/004; C07C 329/00
[52] U.S. Cl. ................... 560/066; 558/270; 558/243
[58] Field of Search ................... 560/66; 158/270, 243

[56] References Cited

U.S. PATENT DOCUMENTS 3,153,010 10/1964 Jenkins et al. .
3,194,791 7/1965 Wilson et al. .
3,408,334 10/1968 Caldwell et al. .
4,129,594 12/1978 Baker et al. ..................... 260/544
4,611,049 9/1986 Kuratsuji et al. .

FOREIGN PATENT DOCUMENTS 0786853 6/1968 Canada .
0029362 5/1981 European Pat. Off. .
0056501 12/1982 European Pat. Off. .
0154506 9/1985 European Pat. Off. .
2939782 3/1981 Fed. Rep. of Germany .
1058341 3/1954 France .
1044015 9/1966 United Kingdom .
1137151 12/1968 United Kingdom .

OTHER PUBLICATIONS

Valade et al., Compte. Rend. 254, p. 3693 (1962).
Chem. Abs. 77:139625r (Abstract of JP 72-27,502) 1972.
Chem. Abs. 53:22096A.
World Patent Index WPI 82-63906E/31.
World Patent Index WPI 81-25669D/15.
Kricheldorf et al., Polym. Bull. 1, 383 (1979).
Chem. Abs. 72:12133v (1970) (Abstract of FR 1,566,217).
Chem. Abs. 70:115281e (1969) (Abstract of Bull. Soc. Chem. Fr. 1969) pp. 262-263).

*Primary Examiner*—Paul J. Killos
*Attorney, Agent, or Firm*—Yuan Chao; Herbert G. Burkard

[57] ABSTRACT

Organic compounds having aromatic ester, thioester, or carbonate groups are prepared by reacting an organometallic reactant where the metal is germanium, tin, lead, gallium, indium, thallium, arsenic, antimony, or bismuth with a suitable second reactant. For example, the ester

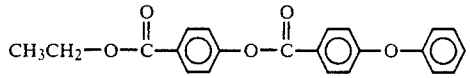

is prepared by reacting the bis-tri-n-butyl tin derivative of ethyl 4-hydroxybenzoate with 4-phenoxybenzoyl chloride.

18 Claims, No Drawings

PREPARATION OF MONOMERS

This application is a divisional of Application Ser. No. 07/204,650, filed July 29, 1988, now U.S. Pat. No. 4,841,094 which is a divisional of Application Ser. No. 06/877,658, filed June 3, 1986, now U.S. Pat. No. 4,777,282, the disclosures of which are incorporated herein by reference.

This invention relates to the preparation of organic compounds and especially to the preparation of monomers for subsequent use in polymerisation reactions.

Known industrial methods for producing monomers, especially aromatic monomers wherein an aromatic group is bonded directly to a functional group such as an ester, thioester or carbonate, often have a number of disadvantages. For example high temperatures are usually required and/or unpleasant solvents such as pyridine are necessary. Aromatic ester monomers, for example can be prepared using a phase-transfer catalysis method, but this method has the disadvantage that two or more recrystallisations of the product are usually necessary in order to obtain a satisfactorily pure monomer.

In a paper by J Valade and M Pereysf entitled 'Étude de la scission de la liaison Sn-O-C dans les monoalcoxytrialcoyétains', Compte. Rend. 254,3693 (1962) there is described a method for making simple aliphatic esters by reacting methoxytributyltin with acetyl chloride or benzoyl chloride, the reaction producing methyl acetate or methyl benzoate. The use of tin in intermediates for making polymers is described in European Patent Publication No. 0,154,506.

In a first aspect the present invention provides a method for the preparation of an organic compound comprising reacting a first compound of the formula:

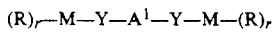

where
- each R is independently a substituted or unsubstituted alkyl or aryl group;
- each r is independently an integer from 1 to 4 inclusive depending upon the element M used;
- each M is independently an element selected from Group IIIB, IVB or VB of the Periodic Table (IUPAC 1965 revision) or a transition metal, excluding carbon, silicon, nitrogen, phosphorus, boron, aluminium and titanium;
- each Y is independently an oxygen atom, a sulphur atom, a substituted nitrogen atom other than

or a substituted phosphorus atom other than

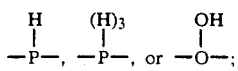

and
- $A^1$ is an aromatic, aliphatic, aromatic/aliphatic, heterocyclic, alicyclic, siloxyl or silane group, with a second compound of the formula:

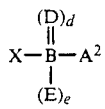

where
- X is a halogen atom or a group capable of reacting with the first compound to eliminate a compound containing M and X;
- B is an atom selected from carbon, phosphorus, sulphur or silicon;
- D is an oxygen or sulphur atom or an amine group;
- d is 1 if B is carbon, zero or 1 if B is phosphorus, zero, 1 or 2 if B is sulphur or zero if B is silicon;
- E is selected from an aromatic group, aliphatic group, OR' or NR'$_2$ if B is phosphorus, or from an aromatic group, aliphatic group or —OR' if B is silicon, where R' is a substituted or unsubstituted alkyl or aryl group;
- e is zero if B is carbon or sulphur, 1 if B is phosphorus or 2 if B is silicon; and
- $A^2$ is an aromatic, aliphatic, aromatic/aliphatic, heterocyclic, alicyclic, siloxyl or silane group, to eliminate the compound $(R)_rMX$ and produce a compound of the formula:

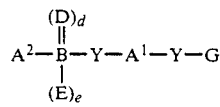

where G is either the group —M—(R)$_r$, or the group

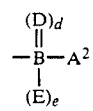

Preferably the stoichiometric ratio of the first compound to the second compound is 1:2 to produce a compound, usually a monomer, of the formula:

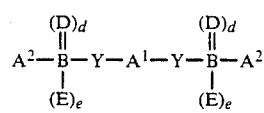

An example of this reaction is as follows:

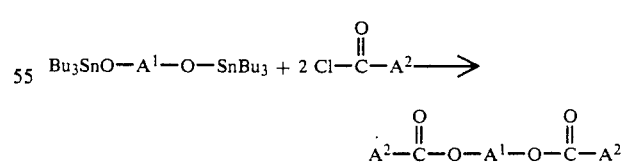

In a second aspect the present invention provides a method for the preparation of an organic compound comprising reacting a first compound of the formula:

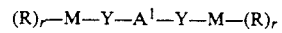

where
- each R is independently a substituted or unsubstituted alkyl or aryl group;

each r is independently an integer from 1 to 4 inclusive depending upon the element M used;

each M is independently an element selected from Group IIIB, IVB or VB of the Periodic Table (IUPAC 1965 revision) or a transition metal, excluding carbon, silicon, nitrogen, phosphorus, boron, aluminium and titanium;

each Y is independently an oxygen atom, a sulphur atom, a substituted nitrogen atom other than

or a substituted phosphorus atom other than

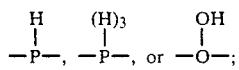

and $A^1$ is an aromatic, aliphatic, aromatic/aliphatic, heterocyclic, alicyclic, siloxyl or silane group, with a second compound of the formula:

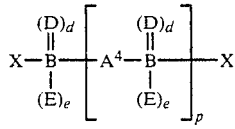

where

X is a halogen atom or a group capable of reacting with the first compound to eliminate a compound containing M and X;

B is an atom selected from carbon, phosphorus, sulphur or silicon;

D is an oxygen or sulphur atom or an amine group;

d is 1 if B is carbon, zero or 1 if B is phosphorus, zero, 1 or 2 if B is sulphur or zero if B is silicon;

E is selected from an aromatic group, aliphatic group, OR' or NR'$_2$ if B is phosphorus, or from an aromatic group, aliphatic group or —OR' if B is silicon, where R' is a substituted or unsubstituted alkyl or aryl group;

e is zero if B is carbon or sulphur, 1 if B is phosphorus or 2 if B is silicon; and p is zero or 1, to eliminate the compound $(R)_rMX$ and produce a compound of the formula:

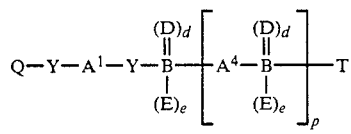

where

Q is the either the group $(R)_rM$-, or the group

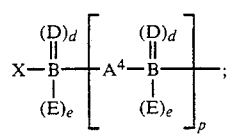

and

T is either the atom or group X, or the group —Y—$A^1$—Y—M—$(R)_r$.

The method according to this second aspect is especially useful when it is desired to produce a monomer having reactive end groups of the type $(R)_rM$-or

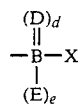

which can then be used directly in polymerisation reactions. An especially preferred monomer is one having acid chloride,

end groups.

When carrying out the method according to the second aspect of the invention, the reaction conditions should be selected so as to prevent a polymerisation reaction between the first and second compounds. Therefore it is preferred to add a solution of the first compound gradually, for example dropwise, to a solution of the second compound. Also it is preferred that the reaction is carried out in a solvent in which the product is substantially insoluble so that the product precipitates out of solution once it is formed.

When p is zero, the second compound being phosgene for example, the reaction produces a compound wherein the group

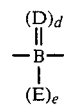

is bonded at both sides to a Y atom, such as in a carbonate. However, it is generally preferred that p is 1 and examples of reactions according to the second aspect of the invention are as follows:

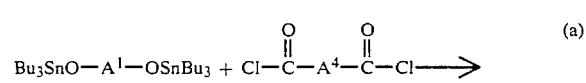

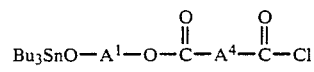

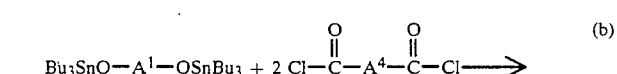

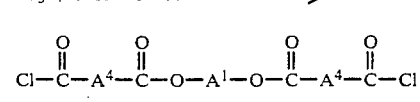

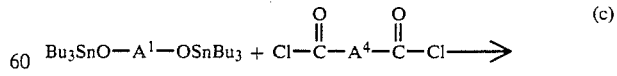

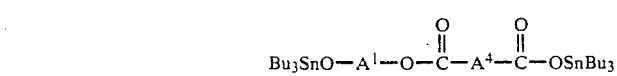

The first compound may also be 'polymeric' and thus a third aspect of the present invention provides a method for the preparation of an organic compound comprising reacting a first compound of the formula:

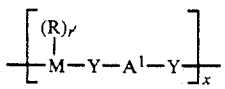

where
- R is independently a substituted or unsubsituted alkyl or aryl group;
- r' is independently zero or an integer from 1 to 3 depending upon the element M used;
- each Y is independently an oxygen atom, a sulphur atom, a substituted nitrogen atom other than

or a substituted phosphorus atom other than

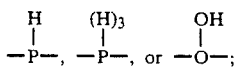

- $A^1$ is an aromatic, aliphatic, aromatic/aliphatic, heterocyclic, alicyclic, siloxyl or silane group, and
- x is an integer greater than 1, with a second compound of the formula:

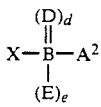

where
- X is a halogen atom or a group capable of reacting with the first compound to eliminate a compound containing M and X;
- B is an atom selected from carbon, phosphorus, sulphur or silicon;
- D is an oxygen or sulphur atom or an amine group;
- d is 1 if B is carbon, zero or 1 if B is phosphorus, zero, 1 or 2 if B is sulphur or zero if B is silicon;
- E is selected from an aromatic group, aliphatic group, OR' or NR'$_2$ if B is phosphorus, or from an aromatic group, aliphatic group or —OR' if B is silicon, where R' is a substituted or unsubstituted alkyl or aryl group;
- e is zero if B is carbon or sulphur, 1 if B is phosphorus or 2 if B is silicon; and
- $A^2$ is an aromatic, aliphatic, aromatic/aliphatic, heterocyclic, alicyclic, siloxyl or silane group, to eliminate the compound

and produce a compound of the formula:

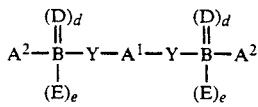

Many different types of compounds can be prepared by the method according to any of the above aspects of the invention. These include, for example, esters, thioesters, amides, thioamides, imides, thioimides, carbonates, thiocarbonates and urethanes, but preferably esters, thioesters, carbonates or thiocarbonates are prepared. Therefore it is preferred that the group

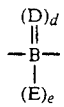

is a carbonyl

group or a thiocarbonyl

group, more preferably a carbonyl group, and that the atom Y is an oxygen or sulphur atom, more preferably an oxygen atom. The methods of the invention are especially advantageous for the preparation of aromatic esters, aromatic thioesters, aromatic carbonates or aromatic thiocarbonates, these being difficult to produce by known commercial methods. By 'aromatic ester', 'aromatic thioester', etc, is meant a compound containing an ester group, thioester group, carbonate group or thiocarbonate group bonded to an aromatic group, for example

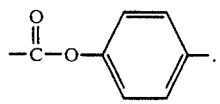

Thus it is preferred that the group $A^1$ in the first compound is partly aromatic and each atom Y is bonded to an aromatic group of $A^1$. It is especially preferred that the compound produced by the reaction contains an ester, thioester, carbonate or thiocarbonate group that is bonded on both sides to an aromatic group; that is to say the resulting compound contains, for example, an aromatic ester group

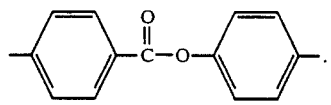

Aromatic esters, thioesters, carbonates or thiocarbonates may be prepared by reacting a difunctional compound containing two (R)$_r$M- groups or a polymeric compound containing the repeat unit

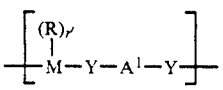

as defined in the above aspects of the invention, or they may be prepared by reacting a monofunctional compound containing only one (R)$_r$M- group with a second compound which may be either mono- or difunctional.

Accordingly, in a fourth aspect the present invention provides a method for the preparation of an aromatic ester, aromatic thioester, aromatic carbonate or aromatic thiocarbonate compound comprising reacting a first compound of the formula:

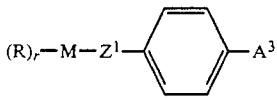

where
each R is independently a substituted or unsubstituted alkyl or aryl group;
r is an integer from 1 to 4 inclusive depending upon the element M used;
M is an element selected from Group IIIB, IVB or VB of the Periodic Table or a transition metal, excluding carbon, silicon, nitrogen, phosphorus, boron, aluminium and titanium;
$Z^1$ is an oxygen or a sulphur atom, and;
$A^3$ is an aromatic, aliphatic, aromatic/aliphatic, heterocyclic, alicyclic, siloxyl or silane group, or a hydrogen atom with a second compound of the formula:

where
X is a halogen atom or a group capable of reacting with the first compound to eliminate M and X;
$Z^2$ is either an oxygen or a sulphur atom; and
J is either the atom or group X, or
  the group $A^2$ where $A^2$ is an aromatic, aliphatic, aromatic/aliphatic, heterocyclic, alicyclic, siloxyl or silane group, or
  the group

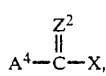

where $A^4$ is an aromatic, aliphatic, aromatic/aliphatic, heterocyclic, alicyclic, siloxyl or silane group,
to eliminate the compound $(R)_rMX$ and produce an aromatic ester, aromatic thioester, aromatic carbonate or aromatic thiocarbonate compound of the formula:

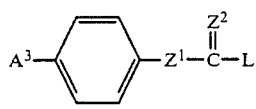

where
L is either the atom or group X, the group $A^2$, the group

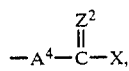

or the group

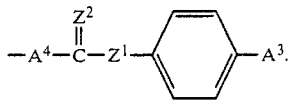

The preferred stoichiometric ratio of the first compound to the second compound according to the fourth aspect of the invention is either 1:1 or 2:1. If a stoichiometric ratio of 1:1 is chosen the second compound may be of the formula:

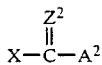

and reaction of the two compounds produces a compound of the formula:

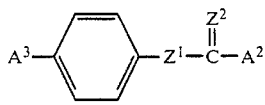

An example of this reaction is:

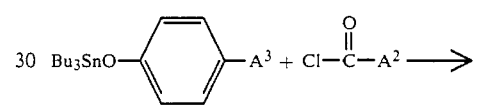

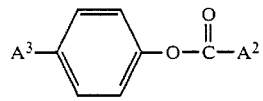

Alternatively the second compound may be of the formula:

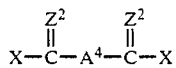

to produce, again using a stoichiometric ratio of first to second compounds of 1:1, a compound of the formula:

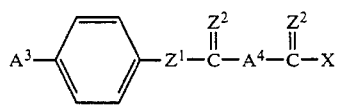

An example of this reaction is:

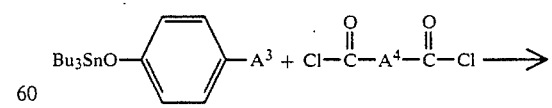

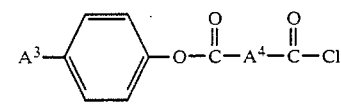

To prevent the product from reacting with a further molecule of the first compound it is preferred that the first and second compounds are reacted together by gradually adding, for example in drops, a solution of the first compound to a solution of the second compound, and also that the reaction is carried out in a solvent in which the compound produced by the reaction is substantially insoluble so that it precipitates out of solution once it is formed.

In another alternative the second compound may be of the formula

to produce a monomer of the formula:

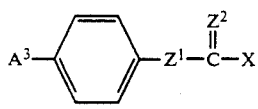

An example of this reaction is:

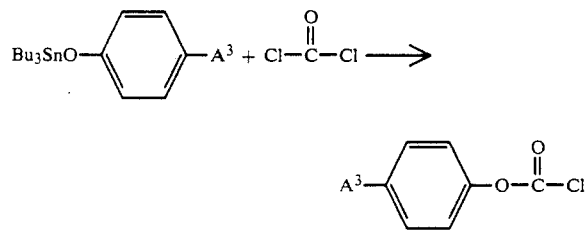

If a stoichiometric ratio of 2:1 is used in the method according to the fourth aspect of the invention, the second compound is preferably of the formula:

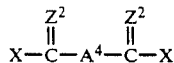

the reaction of first and second compounds then producing a monomer of the formula:

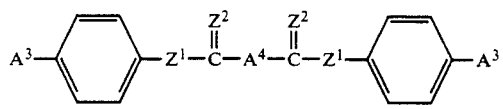

An example of this reaction is:

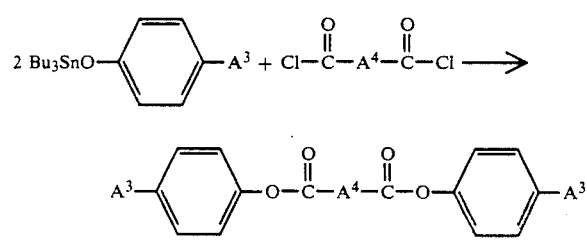

Preferably in the resulting compound the

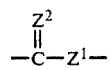

group is bonded on both sides to an aromatic group. Therefore it is preferred that the $A^2$ and $A^4$ groups in the second compounds are each at least partly aromatic, and the

group is bonded to an aromatic group of the $A^2$ or $A^4$ group. Thus the compound produced by the reaction preferably contains a group of the formula

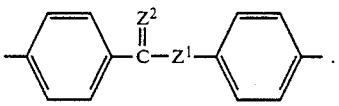

Preferably both $Z^1$ and $Z^2$ are oxygen atoms, the reaction between the first and second compounds therefore producing an aromatic ester.

Hereinafter the description of the invention relates to all aspects of the invention unless otherwise specified.

The method according to the invention is especially advantageous for the preparation of compounds wherein at least one end group, and preferably both end groups, are aromatic, for example a phenyl group. Such compounds are useful as monomers which can be polymerised with one or more other types of monomers, or with themselves, to form, for example, polyesters or polyetheresters. However, the method according to the invention may also be used for the preparation of compounds which are not for subsequent use in polymerisation reactions.

One advantage of the invention is that compounds can often be prepared using relatively low reaction temperatures, usually between −30 degrees and 150 degrees C. (although it is to be understood that higher and lower temperatures can also be used). The use of low temperatures enables thermally sensitive groups to be included in the compound, for example carbon-carbon double and triple bonds.

Another advantage is that the reagents and solvents used in the reaction can be chosen to be relatively non-hazardous. Also the eliminated compounds or by-product, $(R)_rMX$, of the reaction is generally soluble in many solvents, making purification of the resulting compound an unusually easy task. Furthermore this by-product may form a starting reagent for the preparation of the first compound.

Preferably the element M in the first compound is selected from Group IVB of the Periodic Table and is in oxidation state (+4). More preferably M is either tin or germanium, and tin (+4) is especially preferred.

Suitable groups for R include unsubstituted alkyl groups such as methyl, ethyl, propyl, butyl, pentyl, octyl etc., substituted alkyl groups such as benzyl or phenylethyl, or a substituted or unsubstituted aryl group such as phenyl, naphthyl or biphenyl. Preferably, however, R is an alkyl group containing 3 or 4 carbon atoms, an n-butyl group being especially preferred. The number, r, of R groups attached to the element M depends upon the valency of the element M; for example when M is tin (+4) then r is 3. Thus in the first and second aspects of the invention the first compound preferably has the formula $Bu_3Sn-Y-A^1-Y-SnBu_3$, and in the third aspect the first compound preferably has the formula

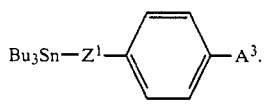

There are many groups suitable for use as the $A^1$, $A^2$, $A^3$ and $A^4$ groups of the first and second compounds. As stated above these are selected from an aromatic, aliphatic, aromatic/aliphatic, heterocyclic, alicyclic, siloxyl or silane group, or for $A^3$ a hydrogen atom. This includes substituted or unsubstituted groups, heteroaromatic, heteroaliphatic and multiple aromatic groups which may be joined by an oxygen or sulphur atom or sulphone, imide or ketone group for example. The $A^1$ and $A^4$ groups are difunctional, the $A^1$ group being bonded at each end to a Y atom or group, and the $A^4$ group being bonded at each end to a

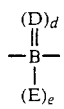

group or

group. The $A^2$ and $A^3$ groups are monofunctional and, as mentioned above, it is preferred that the end of the $A^2$ or $A^3$ group remote from the B or $Z^1$ atom respectively is aromatic. The following list gives examples of suitable groups for the monofunctional $A^2$ and $A^3$ groups. Similar groups are also suitable for $A^1$ and $A^4$ by removal of a hydrogen atom, thus providing a difunctional group.

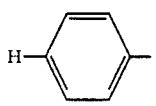
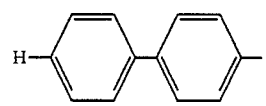
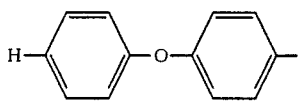
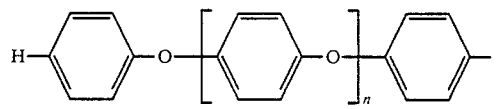
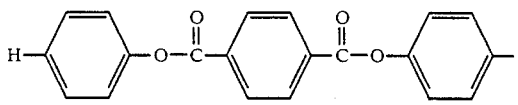
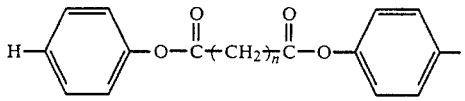
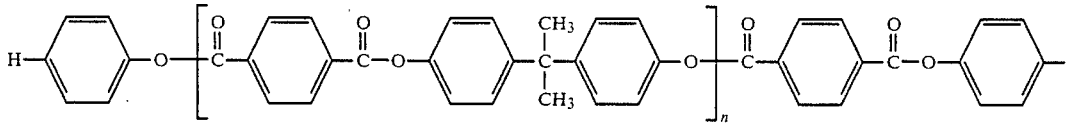
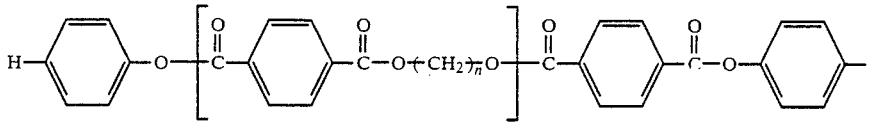
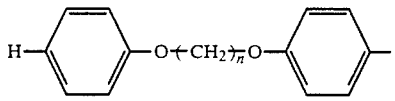
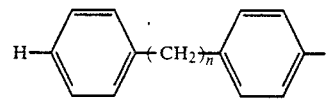
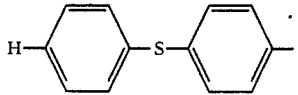
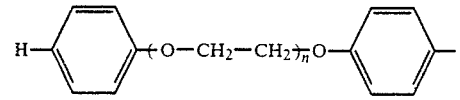
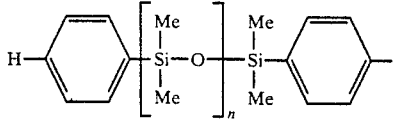
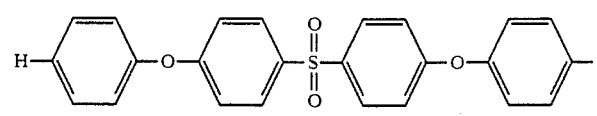

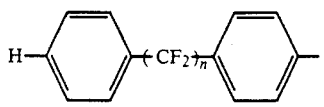 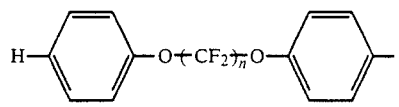

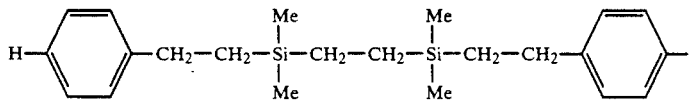

These examples listed for the A groups are bonded to the B or Y atom with an aromatic carbon atom. However groups may also be chosen for any one of the A groups wherein an aliphatic carbon atom or a silicon atom is bonded to the Y atom of the first compound or the B or C atom of the second compound as appropriate. Also the $A^2$ and $A^4$ groups may contain an oxygen, nitrogen or sulphur for example which bonds to the B or C atom respectively in the second compound in the first, second or third aspects of the invention.

Typical solvents used in the process of the present invention include, for example, chloroform, xylene, toluene, tetrahydrofuran, chlorobenzene, 1,2-dichloroethane, benzophenone, diphenylsulphone, or mixtures thereof, although it should be remembered that when the compound produced has end groups of the formula $(R)_rM-$ or $-X$ then the solvent chosen should be one in which the compound produced is substantially insoluble.

Once the compound has been isolated it is possible for the by-product to be easily removed, for example by extraction with acetone, hexane, methanol or other simple solvents which do not affect the resulting compound adversely. The by-product can then be recovered by distillation or crystallisation for example.

There are a number of possible routes for preparing the first compound for the method according to the invention. In the first aspect of the invention the first compound, for example $Bu_3SnO-A^1-OSnBu_3$, may be prepared by reaction of $Bu_3SnOMe$ with $HO-A^1-OH$. Similarly in the second aspect of the invention the first compound, for example

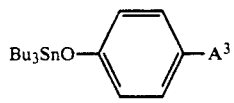

may be prepared by reaction of $Bu_3SnOMe$ with

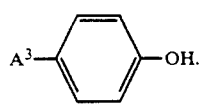

The invention will now be illustrated by the following examples.

EXAMPLE 1

To 400 mls of xylene was added 50 g of thiophenol and 135.3 g of bis(tributyltin)oxide. The reaction mixture was heated to boiling and water of reaction removed using a Dean-Stark head. After all the water had been removed heating was discontinued and when refluxing had subsided 46.06 g of isophthaloyl dichloride added. This produced a slight yellowing of the solution. The mixture was then heated to reflux for 3 hours and then allowed to cool. The colourless crystalline product was collected by filtration, washed with cold toluene and dried. A further crop of crystals was obtained by concentrating the mother liquors.

Yield was 76.5 g, 96%,

The product was identified as

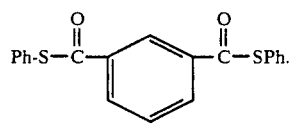

The analogous terephthaloyl product was prepared by repeating the above reaction, replacing the isopthaloyl dichloride with terephthaloyl dichloride.

EXAMPLE 2

To 225 mls of xylene was added 5.50 g of hydroquinone and 29.81 g of bis(tributyltin)oxide. The reaction mixture was heated to boiling and water of reaction removed using a Dean-Stark head. After all the water had been removed heating was discontinued and when refluxing has subsided 24.43 g of 4-phenoxybenzoylchloride added. The mixture was then heated to reflux for 3 hours and then allowed to cool. The colourless crystalline product was collected by filtration, washed with cold toluene and dried. A further crop of crystals was obtained by concentrating the mother liquor.

Yield was 24.0 g, 90%.

The product was identified as

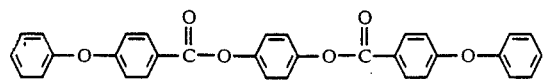

This monomer may be reacted with a mixture of terephthaloyl and isophthaloyl chlorides in 1,2-dichloroethane together with N,N-dimethylformamide and aluminium chloride to produce a polymer of the repeat unit:

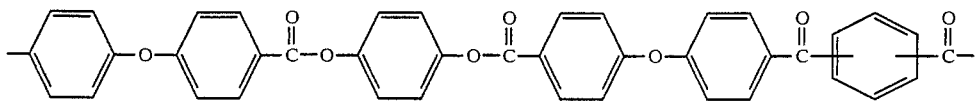

EXAMPLE 3

To 125 mls of xylene was added 6.0 g of phenoxyphenol and 9.60 g of bis(tributyltin)oxide. The reaction mixture was heated to boiling and water of reaction removed using a Dean-Stark head. After all the water had been removed heating was discontinued and when refluxing had subsided 3.27 g of terephthaloyl chloride added. The mixture was heated to reflux for 3 hours and then allowed to cool. The colourless crystalline product was collected by filtration, washed with cold toluene and dried. A further crop of crystals was obtained by concentrating the mother liquor.

Yield 7.5 g, 91%.

The product was identified as

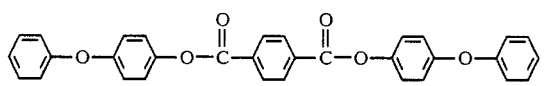

The analogous isophthaloyl product was prepared by repeating the above reaction, replacing the terephthaloyl dichloride with isophthaloyl dichloride.

This monomer may be reacted with a mixture of terephthaloyl and isophthaloyl chloride in 1,2-dichloroethane together with N,N-dimethylformamide and aluiminium chloride to produce a polymer of the repeat unit:

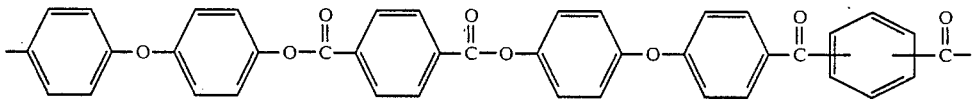

EXAMPLE 4

To 500 mls of toluene was added 15.32 g of bisphenol A and 43.1 g of tributyltinmethoxide. The reaction was heated to boiling and using a fractionating column methanol was removed. When all the methanol had been removed heating was discontinued and when refluxing had subsided 18.86 g of benzoylchloride added. The mixture was then heated to reflux for 3 hours and then allowed to cool. The colourless crystalline product was collected by filtration, washed with cold toluene and dried. A further crop of crystals was obtained by concentrating the mother liquors.

Yield 27.2 g, 93%.

The product was identified as

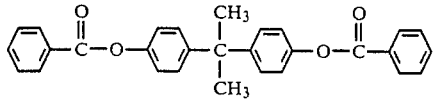

The above reaction was repeated a number of times, the bisphenol A being replaced in each repeated reaction with a different compound as indicated below:

a) replacing bisphenol A with hydroquinone to produce the monomer

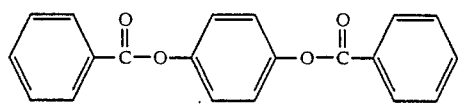

b) replacing biphenol A with methylhydroquinone to produce the monomer

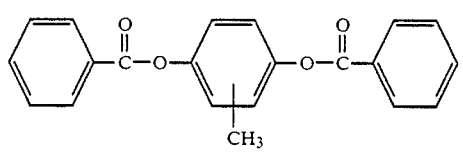

c) replacing bisphenol A with 4,4'-dihydroxydiphenyl ether to produce the monomer

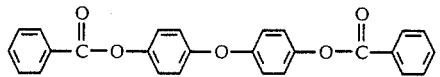

d) replacing bisphenol A with 4,4'-dihydroxybiphenyl to produce the monomer

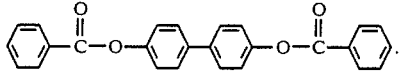

EXAMPLE 5

To 100 mls of xylene was added 3.1 g of methylhydroquinone and 14.70 g of bis(tributyltin)oxide. The reaction mixture was heated to boiling and water of reaction removed using a Dean-Stark head. After all the water had been removed heating was discontinued and when refluxing had subsided 9 g of 4-n-propylbenzoyl chloride added. The mixture was then heated to reflux for 3 hours. The pale yellow solution was concentrated on a rotary evaporator leaving a yellow oil. This was dissolved in methylcyclohexane and cooled to −15° C. to give a colourless, crystalline product.

Yield 9 g, 86%.

The product was identified as

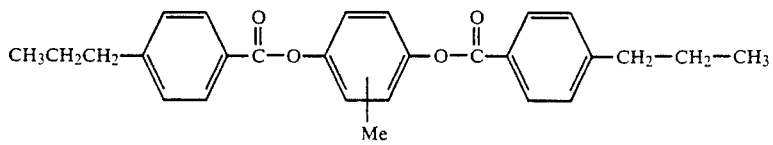

EXAMPLE 6

To 200 mls of toluene was added 13.84 g of 4-bromophenol and 23.84 g of bis(tributyltin)oxide. The reaction mixture was heated to boiling and water of reaction removed using a Dean-Stark head. After all the water had been removed heating was discontinued and when refluxing had subsided 8.12 g of terephthaloyl chloride added. The mixture was then refluxed for two hours and then allowed to cool. The white crystalline product was collected by filtration, washed with cold toluene and dried. A further crop of crystals was obtained by concentrating the mother liquor.

Yield 17.68 g, 93%.

The product was identified as,

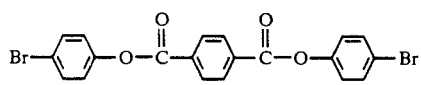

EXAMPLE 7

To 150 m mls of toluene was added 6.61 g of hydroquinone and 35.76 g of bis(tributyltin)oxide. The reaction mixture was heated to boiling and water of reaction removed using a Dean-Stark head. After all the water had been removed heating was discontinued and when refluxing had subsided 19.03 g of p-fluorobenzoyl chloride added. The mixture was refluxed for one hour and then allowed to cool. The white crystalline product was collected by filtration, washed with cold toluene and dried. A further crop of crystals was obtained by concentrating the mother liquor.

Yield 19.89 g 93.5%.

The product was identified as,

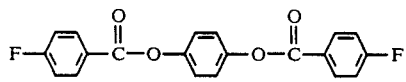

EXAMPLE 8

To 150 m mls toluene was added 9.97 g of ethyl-4-hydroxybenzoate and 17.88 g of bis(tributyltin)oxide. The reaction mixture was heated to boiling and water of reaction removed using a Dean-Stark head. After all the water had been removed heating was discontinued and when refluxing had subsided 27.92 g of 4-phenoxybenzoyl chloride added. The mixture was refluxed for one hour and then allowed to cool. No precipitate formed on cooling. The toluene was removed under reduced pressure and replaced by hexane. After cooling to −18° C. a white crystalline product was obtained. A further crop of crystals was obtained by concentrating the mother liquor. This material was very soluble at room temperature in a number of solvents.

Yield 37.40 g 86%.

The product was identified as

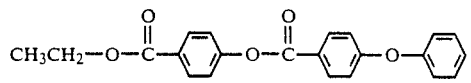

EXAMPLE 9

To 150 mls of toluene was added 5.51 g of hydroquinone and 29.80 g of bis(tributyltin)oxide. The reaction mixture was heated to boiling and water of reaction removed using a Dean-Stark head. After allowing to cool the solution was transferred to a dropping funnel equipped with a pressure equalising side arm. This solution was then slowly added to an almost refluxing solution of 30.45 g of terephthaloyl chloride in 150 mls of toluene. After the addition was complete the mixture was refluxed for 2 hours and then allowed to cool. The white crystalline product was collected by filtration washed with cold toluene and dried.

Yield 20 g 88%.

The product was identified as

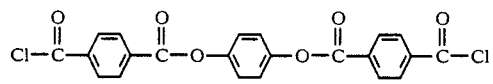

EXAMPLE 10

To 200 ml of toluene was added 20.43 g of 4-phenylphenol and 35.76 g of bis(tributyltin) oxide. The reaction mixture was heated to boiling and water of reaction removed using a Dean-Stark head. After all the water had been removed the reaction mixture was allowed to cool. When cool the solution was transferred to a dropping funnel fitted with a pressure equalising side arm. This solution was then slowly added to a warm solution of 48.72 g of terephthaloyl chloride in 150 mls of toluene. After the addition was complete the mixture was heated to reflux for one hour and then allowed to cool. The pale yellow crystalline product was collected by filtration washed with cold toluene and dried.

Two products were identified:

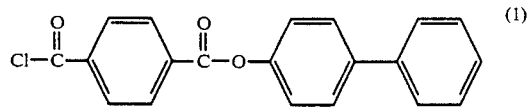

34.29 g, 85% yield.

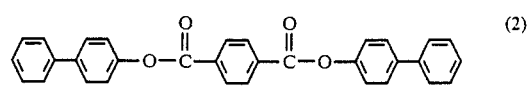

10% yield.

The product

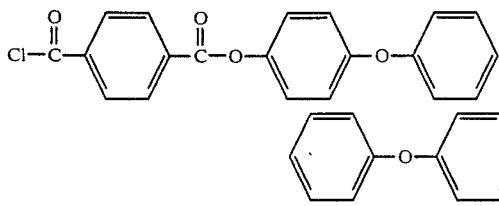

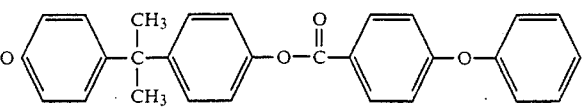

was prepared in a similar manner.

EXAMPLE 11

To 200 mls of toluene was added 16.52 g of hydroquinone and 89.41 g of bis(tributyltin)oxide. The reaction mixture was heated to boiling and water of reaction removed using a Dean-Stark head. After all the water had been removed heating was discontinued. One the temperature of the solution had droped to 80° C. a solution of 12.18 g of terephthaloyl chloride in 50 mls of toluene was slowly added over 45 minutes. After the addition was complete the whole mixture was refluxed for 2 hours. Once cool the toluene was removed and replaced with 200 mls of methanol plus 20 mls of a 50% solution of a hydrochloric acid. The white solid was collected by filtration and washed with 300 mls of methanol at 50° C.

Yield 16.40 g 80%.

The product was identified as

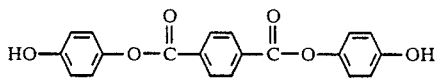

EXAMPLE 12

To 150 mls of toluene was added 10 g of 4-phenoxyphenol and 16.00 g of bis(tributyltin)oxide. The reaction mixture was heating to boiling and water of reaction removed using a Dean-Stark head. After all the water had been removed heating was discontinued and the mixture allowed to cool to room temperature. Once cool a solution of 2.66 g of phosgene in 18 mls of toluene was slowly added. Upon completion of the addition the mixture was stirred at room temperature for 1 hour and then at reflux for 1 hour. After cooling to −18° C. the white crystalline solid was collected by filtration washed with cold toluene and dried.

Yield 9.6 g 89%.

The product was identified as

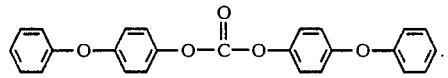

EXAMPLE 13

To 200 mls of toluene was added 20 g of bisphenol A and 21.80 g of dibutyltin oxide. The reaction mixture was heated to boiling and water of reaction removed using a Dean-Stark head. After all the water had been removed heating was discontinued and the viscous solution allowed to cool to 90° C. To this solution was added 40.73 g of 4-phenoxybenzoyl chloride and the mixture heated to reflux for 1 hour. After cooling the white crystalline product was collected by filtration, washed with cold toluene and dried.

Yield 49.71 g 91.5%.

The product was identified as

I claim:

1. A method for the preparation of an aromatic ester, aromatic thioester, aromatic carbonate, or aromatic thiocarbonate compound comprising reacting a first compound of the formula:

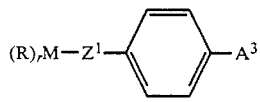

where
each R is independently a substituted or unsubstituted alkyl or aryl group
r is an integer from 1 to 4 inclusive depending upon the element M used;
M is an element selected from the group consisting of germanium, tin, lead, gallium, indium, thallium, arsenic, antimony, and bismuth;
$Z^1$ is an oxygen or sulphur atom; and
$A^3$ is an aromatic, aliphatic, aromatic/aliphatic, heterocyclic, alicyclic, siloxyl or siloxane group, or a hydrogen atom
with a second compound of the formula

where
X is a halogen atom or a group capable of reacting with the first compound to eliminate a compound containing M and X;
$Z^2$ is either an oxygen or a sulphur atom; and
J is either X or the group $A^2$ where $A^2$ is an aromatic, aliphatic, aromatic/aliphatic, heterocyclic, alicyclic, siloxyl, or silane group, or the group

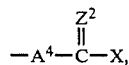

where $A^4$ is an aromatic, aliphatic, aromatic/aliphatic, heterocyclic, alicyclic, siloxyl or silane group,
the proportions of the reactants and/or reaction conditions being selected to prevent polymerization and to eliminate the compound $(R)rMX$ and produce an aromatic ester, aromatic thioester, aromatic carbonate or aromatic thiocarbonate compound of the formula:

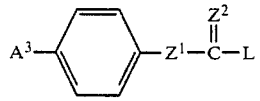

where L is X, the group $A^2$, the group

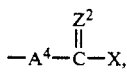

or the group

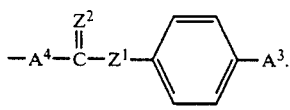

2. A method according to claim 1 wherein the reaction is carried out in a solvent in which the product is substantially insoluble so that the product precipitates out of solution as it is formed.

3. A method according to claim 1 wherein $Z^1$ is an oxygen atom.

4. A method according to claim 1 or 3 wherein $Z^2$ is an oxygen atom.

5. A method according to any one of claims 1 to 4 wherein the stoichiometric ratio of the first compound to the second compound is 1:1.

6. A method according to claim 5 wherein the second compound is of the formula:

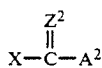

and the first and second compounds react to produce an aromatic ester, aromatic thioester, aromatic carbonate or aromatic thiocarbonate compound of the formula:

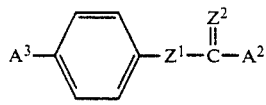

7. A method according to claim 6 wherein the group

is bonded to an aromatic group of $A^2$.

8. A method according to claim 5 wherein the second compound is of the formula:

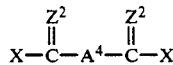

and the first and second compounds react to produce an aromatic ester, aromatic thioester, aromatic carbonate or aromatic thiocarbonate of the formula:

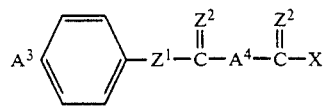

9. A method according to claim 8 wherein the first and second compounds are reacted together by gradually adding a solution of the first compound to a solution of the second compound.

10. A method according to claim 1 wherein the first and second compounds are reacted together in a solvent in which the compound produced by the reaction is substantially insoluble to that the compound is precipitated substantially as soon as it is produced.

11. A method according to any one of claim 1 to 4 wherein the second compound is of the formula:

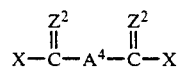

and the first and second compounds are reacted together in a stoichiometric ratio of 2:1 to produce an aromatic ester, aromatic thioester, aromatic carbonate or a aromatic thiocarbonate of the formula:

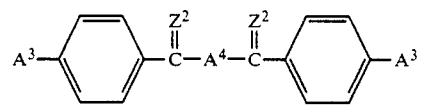

12. A method according to claim 8 wherein the group $A^4$ is at least partly aromatic and the groups

are each bonded to an aromatic group of $A^4$.

13. A method according to claim 12 wherein M is tin.

14. A method according to claim 12 wherein r is 3.

15. A method according to claim 1 wherein R is a butyl group.

16. A method according to any one of the preceding claims wherein X is a halogen atom.

17. A method according to claim 16 wherein x is a chlorine atom.

18. A method according to claim 12 wherein M is tin, lead, or germanium.

* * * * *